United States Patent
Schomacker et al.

(10) Patent No.: US 11,110,294 B2
(45) Date of Patent: Sep. 7, 2021

(54) COOLING SYSTEM FOR TISSUE TREATMENT SYSTEM WITH BOTH TISSUE AND LIGHT SOURCE COOLING

(71) Applicant: Candela Corporation, Wayland, MA (US)

(72) Inventors: Kevin Schomacker, Maynard, MA (US); Dima Dubitsky, Natick, MA (US)

(73) Assignee: Candela Corporation, Marlborough, MA (US)

( * ) Notice: Subject to any disclaimer, the term of this patent is extended or adjusted under 35 U.S.C. 154(b) by 147 days.

(21) Appl. No.: 16/569,693

(22) Filed: Sep. 13, 2019

(65) Prior Publication Data
US 2021/0077823 A1   Mar. 18, 2021

(51) Int. Cl.
*A61N 5/06* (2006.01)
*A61B 18/20* (2006.01)
*A61F 7/00* (2006.01)
*A61B 18/00* (2006.01)
(Continued)

(52) U.S. Cl.
CPC .......... *A61N 5/0616* (2013.01); *A61B 18/203* (2013.01); *A61F 7/007* (2013.01);
(Continued)

(58) Field of Classification Search
CPC ........ A61B 18/203; A61B 2018/00023; A61B 2018/00047; A61B 2015/00452;
(Continued)

(56) References Cited

U.S. PATENT DOCUMENTS 5,422,899 A * 6/1995 Freiberg .................. H01S 3/042
                                                                  372/25
5,849,029 A * 12/1998 Eckhouse ............ A61B 18/203
                                                                  607/104
(Continued)

FOREIGN PATENT DOCUMENTS

WO   2018185773 A1   10/2018

OTHER PUBLICATIONS

Partial International Search Report in PCT/US2020/050074 dated Nov. 26, 2020.
(Continued)

*Primary Examiner* — Jonathan T Kuo
(74) *Attorney, Agent, or Firm* — Manelli Selter PLLC; Edward Stemberger (57) ABSTRACT

A tissue treatment system includes an applicator connected with a base unit. The applicator includes a light source to generate light energy. A light guide directs the light energy to biological tissue and is configured to contact biological tissue. A thermoelectric cooler has a cold side and a hot side, with the cold side being associated with the light guide. A hot side plate is mounted to the hot side of the thermoelectric cooler. A first fluid passage is between the reservoir and the hot side plate to deliver cooling fluid over the hot side plate to chill the cold side of the thermoelectric cooler and cool the light guide and biological tissue. A second fluid passage is associated with the light source to direct cooling fluid to the light source prior to being returned to the reservoir. The first and second fluid passages define a single cooling fluid circulation loop.

23 Claims, 7 Drawing Sheets

(51) Int. Cl.
*A61N 1/40* (2006.01)
*A61N 5/067* (2006.01)

(52) U.S. Cl.
CPC ............ *A61B 2018/00023* (2013.01); *A61B 2018/00452* (2013.01); *A61F 2007/0052* (2013.01); *A61F 2007/0056* (2013.01); *A61N 1/403* (2013.01); *A61N 2005/067* (2013.01); *A61N 2005/0644* (2013.01)

(58) Field of Classification Search
CPC .... A61B 2018/0047; A61B 2018/1807; A61B 18/20–18/28; A61F 2007/0052; A61F 2007/0056; A61F 7/007; A61F 7/00–2007/126; A61N 1/403; A61N 2005/0644; A61N 2005/067; A61N 5/0616; A61N 5/06–2005/073
See application file for complete search history.

(56) References Cited

U.S. PATENT DOCUMENTS

| | | | |
|---|---|---|---|
| 7,097,656 B1* | 8/2006 | Akopov | A61B 18/203 606/10 |
| 7,703,458 B2* | 4/2010 | Levernier | A61B 18/203 128/898 |
| 8,474,463 B2* | 7/2013 | Levernier | A61B 18/203 128/898 |
| 2002/0173780 A1* | 11/2002 | Altshuler | A61B 18/203 606/9 |
| 2005/0107852 A1* | 5/2005 | Levernier | A61B 18/203 607/89 |
| 2009/0182397 A1* | 7/2009 | Gustavsson | A61N 5/0613 607/88 |
| 2010/0222853 A1* | 9/2010 | Levernier | A61B 18/203 607/89 |
| 2017/0304645 A1 | 10/2017 | Schomacker et al. | |
| 2018/0140866 A1 | 5/2018 | Daly et al. | |
| 2019/0254744 A1* | 8/2019 | Miller | A61B 18/22 |

OTHER PUBLICATIONS

International Search Report and Written Opinion in PCT/US2020/050074 dated Feb. 5, 2021.

* cited by examiner

FIG. 8

COOLING SYSTEM FOR TISSUE TREATMENT SYSTEM WITH BOTH TISSUE AND LIGHT SOURCE COOLING

FIELD

The embodiment relates to a tissue treatment system such as for hair removal treatment and/or laser skin treatment and, more particularly, to a cooling system for a tissue treatment system that provides a single cooling system to cool both the tissue being treated and the light source of the tissue treatment system.

BACKGROUND

A conventional applicator or hand-piece for a tissue treatment system requires coolant flow to remove heat from the light source of the system and, in some cases, from the tissue being treated such as for pre-cooling prior to delivering the treatment pulse or for post cooling to remove added heat from the treatment pulse.

Separate coolant systems are used in conventional treatment systems requiring cooling for both the light source and the tissue. Thus, these systems typically include four coolant lines in a single umbilical cable that is connected between the applicator and a source of coolant. There are two delivery coolant lines and two return coolant lines. The first delivery coolant line delivers coolant from the coolant source to structure that engages and thus cools treated tissue. A first return coolant line returns the coolant from the structure back to the coolant source. A second delivery coolant line delivers coolant from the coolant source to be near the light source, such as a flashlamp, a flashlamp and laser rod, or a laser diode, to cool the light source and maintain the light source at a desired temperature. A second coolant return line returns the coolant that cools the light source back to the coolant source. This conventional coolant system with four coolant lines results in a bulky umbilical cable that is awkward for an operator to handle and such system increases material and assembly costs.

Thus, there is a need to provide cooling system for a tissue treatment system having only two coolant lines that can cool both the treated tissue and the light source.

SUMMARY

An objective of the embodiment is to fulfill the need referred to above. In accordance with the principles of an embodiment, this objective is achieved by a tissue treatment system including a base unit having a power source and a reservoir for containing a cooling fluid. An applicator is connected with the base unit via a cable. The applicator includes a tissue cooling element constructed and arranged to engage biological tissue for treatment, the tissue cooling element including channel structure there-through; and a light source powered by the power source and constructed and arranged to generate light energy directed to the tissue cooling element and thus to the biological tissue. A first fluid passage is provided between the reservoir and the channel structure of the tissue cooling structure to deliver the cooling fluid through the tissue cooling structure. A second fluid passage is provided between the channel structure and the reservoir to return the cooling fluid to the reservoir. The second fluid passage is associated with the light source to direct cooling fluid to the light source prior to being returned to the reservoir. The first and second fluid passages define a single cooling fluid circulation loop to cool both the tissue cooling element and the light source. A portion of each of the first and second fluid passages is disposed in the cable.

In accordance with another aspect of an embodiment, a tissue treatment system includes a base unit having a power source and a reservoir for containing a cooling fluid. An applicator is connected with the base unit via a cable. The applicator includes a light source powered by the power source and constructed and arranged to generate light energy; a light guide disposed adjacent to the light source for directing the light energy to biological tissue; at least one thermoelectric cooler having a cold side and a hot side, the cold side being associated with the light guide; and at least one hot side plate mounted to the hot side of the thermoelectric cooler. A first fluid passage structure is provided between the reservoir and the hot side plate to deliver cooling fluid over the hot side plate to chill the cold side of the thermoelectric cooler and thus cool the light guide to cool the biological tissue. A second fluid passage structure is provided between the hot side plate and the reservoir to return the cooling fluid to the reservoir. The second fluid passage structure is associated with the light source to direct cooling fluid to the light source prior to being returned to the reservoir. The first and second fluid passage structures define a single cooling fluid circulation loop to cool both the light guide and the light source. A portion of each of the first and second fluid passage structure is disposed in the cable.

In accordance with yet another aspect of an embodiment, a method of cooling a tissue treatment system is provided. The system includes a base unit having a power source and a reservoir for containing a cooling fluid. An applicator is connected with the base unit via a cable with the applicator including a light source powered by the power source and constructed and arranged to generate light energy, and a tissue cooling element disposed adjacent to the light source for directing the light energy to biological tissue. A portion of the tissue cooling element is configured to contact the biological tissue. The method provides first fluid passage structure from the reservoir and extending to be associated with the tissue cooling element. The cooling fluid is delivered through the first passage structure to chill the tissue cooling element and thus cool the biological tissue. Second fluid passage structure is provided from the tissue cooling element to the reservoir to return the cooling fluid to the reservoir. The second fluid passage structure is associated with the light source. Prior to returning the cooling fluid to the reservoir, the cooling fluid is directed through the second passage structure to the light source to cool the light source. The first and second fluid passage structures define a single cooling fluid circulation loop to cool both the tissue cooling element and the light source. A portion of each of the first and second fluid passage structure is disposed in the cable.

Other objectives, features and characteristics of the present embodiment, as well as the methods of operation and the functions of the related elements of the structure, the combination of parts and economics of manufacture will become more apparent upon consideration of the following detailed description and appended claims with reference to the accompanying drawings, all of which form a part of this specification.

DETAILED DESCRIPTION OF THE EXEMPLARY EMBODIMENTS

Figure 1:
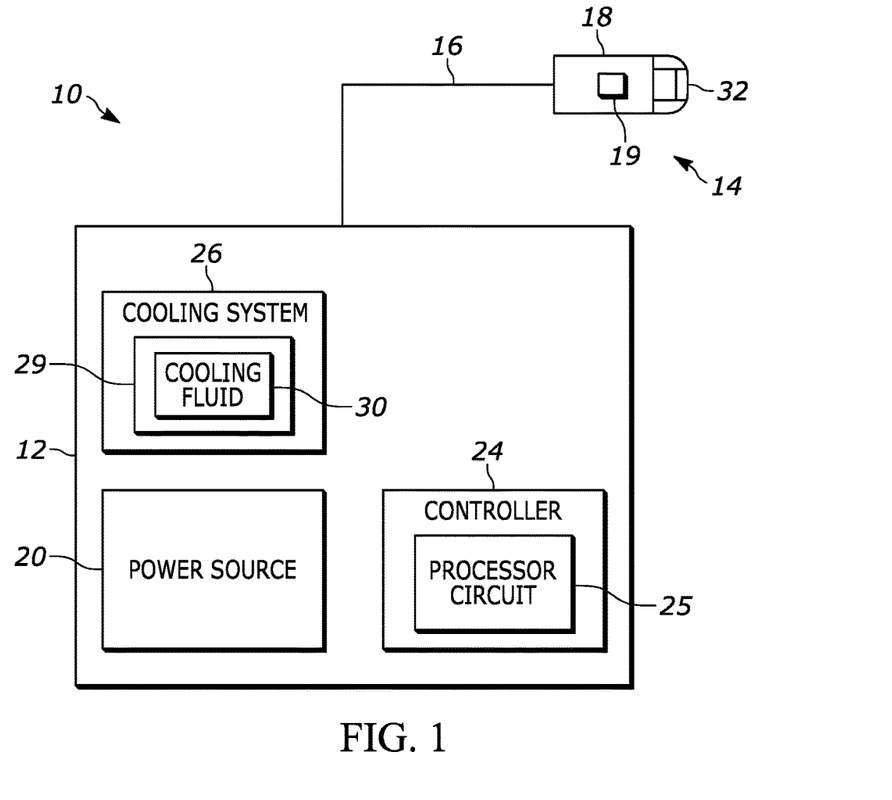
FIG. 1 is a schematic illustration of a tissue treatment system provided in accordance with an embodiment.

With reference to FIG. 1, an embodiment of a tissue treatment system is shown, generally indicated at 10, for treating biological tissue. The system 10 can be used to non-invasively deliver radiation to target biological tissue such as the skin or hair. The system 10 includes a base unit 12 and a delivery system, generally indicated at 14. In the illustrated embodiment, the delivery system 14 includes an umbilical cable 16 and an applicator 18. The applicator 18 can be a hand-held device, such as a handpiece, which can be held or manipulated by a user to irradiate the target tissue via a light source 19 provided in the applicator 18. In one embodiment, light energy provided by the light source 19 is directed via the delivery system 14 to the target tissue.

The base unit 12 is coupled to the umbilical cable 16, which is connected to a delivery module 14. The base unit 12 includes a power source 20 that supplies power to various system components, including the light source 19. The light source 19 can be a flashlamp used in intense pulsed light (IPL) systems, a flashlamp and laser rod used in solid state laser systems, or a diode laser used in diode laser systems for emitting light energy such as a light beam L (FIG. 3) to the target tissue. A foot pedal (not shown) or finger switch on the applicator 18 can be employed to control the light source 19. The base unit 12 also includes a controller 24 coupled with the light source 19 and which can be coupled to a user interface. The controller 24 includes a processor circuit 25.

Figure 2:
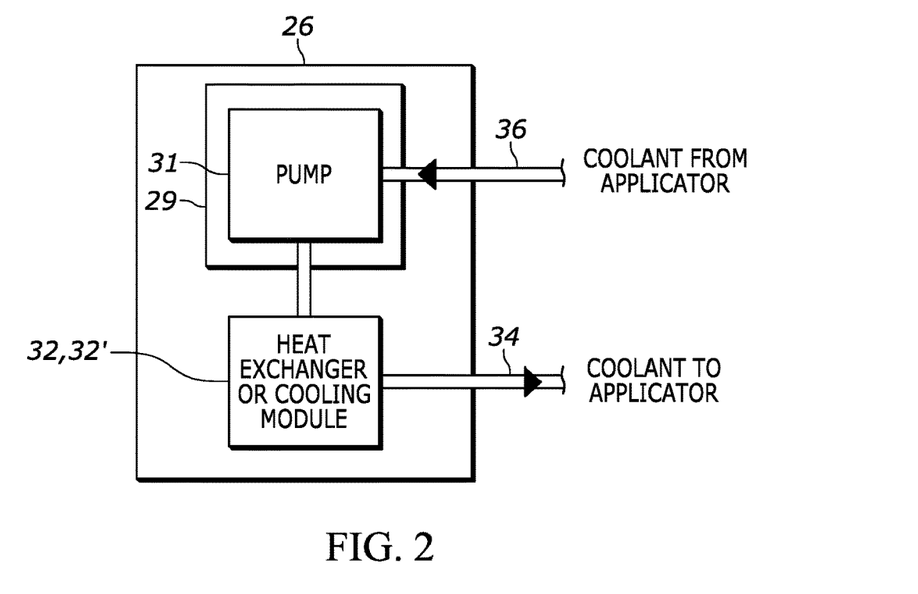
FIG. 2 is an enlarged view of a portion of the cooling system of the tissue treatment system FIG. 1.

The base unit 12 includes a cooling system 26 that includes a reservoir 29 containing a coolant or cooling fluid 30 such as water or antifreeze. Antifreeze should be chosen to have minimal absorption to light energy or designed to work with fluid channels where light passes through sapphire only and not through antifreeze. With reference to FIG. 2, the cooling system 26 includes a pump 31, preferably in reservoir 29, which pumps the cooling fluid 30 through a heat exchanger 32 which is delivered to the applicator 18 via a first fluid passage 34 and returned to the pump 31 via a second fluid passage 36. Portions of fluid passages 34 and 36 are disposed in the umbilical cable 16. The heat exchanger 32 is preferably a radiator combined with a fan to keep the cooling fluid 30 at a temperature close to or above ambient temperature. Instead of providing a heat exchanger 32, a cooling module 32' can be provided. The cooling module 32' can be a thermoelectric cooling module or a compressor refrigerator system to maintain the cooling fluid 30 at a temperature below the ambient temperature.

Figure 3:
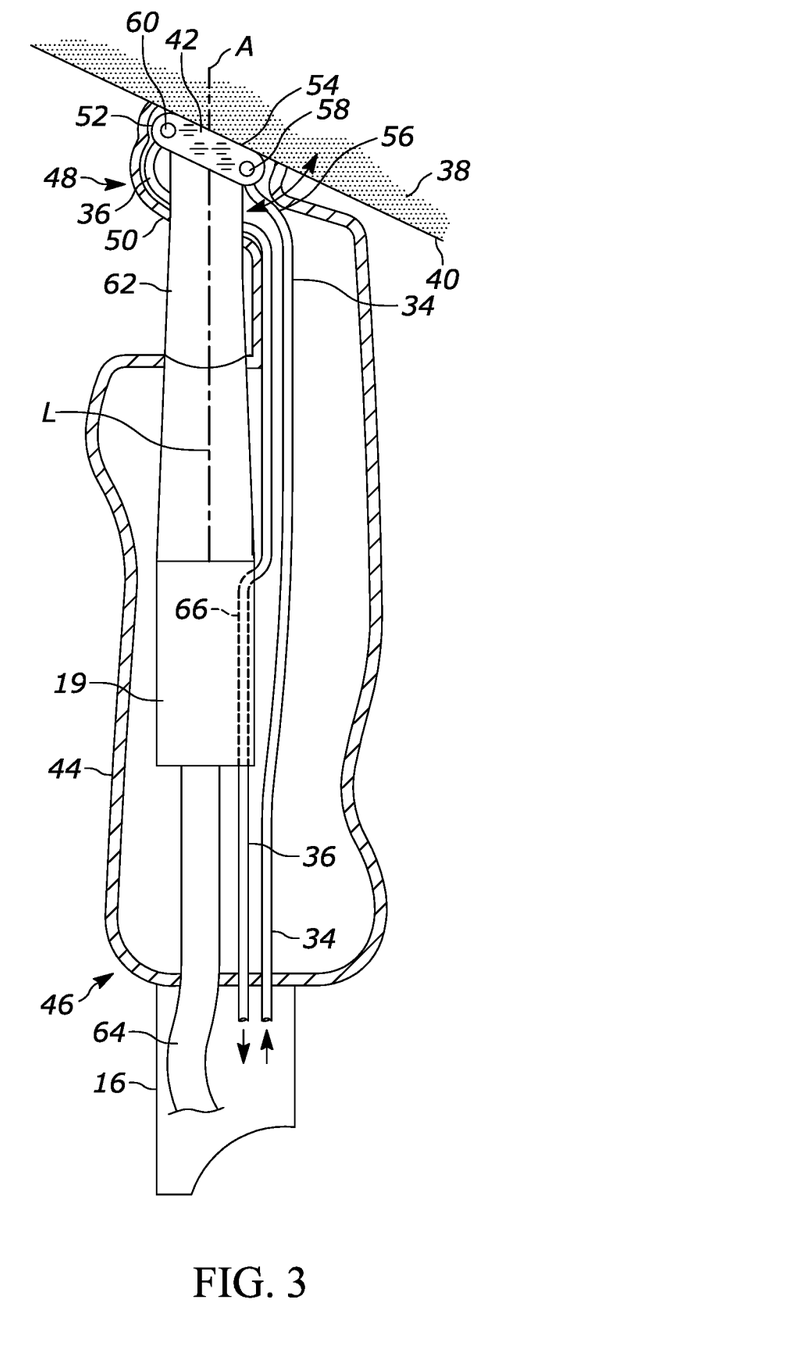
FIG. 3 is a side, partial sectional view of an applicator of the tissue treatment system of FIG. 1, shown engaging tissue being treated.

With reference to FIG. 3, tissue 38 located in a tissue treatment plane 40 is cooled by a portion of the applicator 18 being in contact with the tissue 38 located in the treatment plane 40. Absence of effective cooling of the epidermis while heating the dermis and deeper skin layers during the course of light (laser) energy treatments can cause undesired pain to the treated subject and potentially undesired skin injury.

The applicator 18 provides contact cooling to the tissue by conduction of heat from the tissue 38 to a tissue cooling element or chilled tip 42 placed directly onto the tissue as will be explained below. As shown in FIG. 3, the applicator 18 includes a housing 44 with a proximal end 46 and a distal end 48. A support structure 50 is terminated by a frame 52 that extends from distal end 48. Support structure 50 is angled to applicator 18 axis of symmetry A or off normal relative to axis of symmetry A of the applicator and improves line of sight to the skin treatment plane 40 or skin area 46 to be treated. The compliment of angle 56 at which support structure 50 is angled could be 10 to 30 degrees and usually the angle could be about 15 degrees.

The chilled tip 42 can be in the form of a window that is preferably made of transparent sapphire or quartz. The frame 52 of the support structure 50 includes a slot of rectangular or oval shape that receives the chilled tip 42. For applications that combine RF energy with light energy to obtain a treatment effect, support structure 50 is made of metal or other material supporting good heat or cold conducting properties, and RF electrical conducting properties. The chilled tip 42 includes channel structure in the form of two cooling fluid channels 58 and 60 that communicate with each other. Typically, cooling fluid 30 is delivered through the first passage structure positioned on one side of the support structure 50, and is passed through both channels 58 and 60, then returned via the second passage structure positioned on the other side of support structure 50. Alternatively, channel 58 can be considered an inlet channel and channel 60 can be considered an exit channel. Cooling fluid channels 58 and 60 provided through the chilled tip 42 are in fluid communication with fluid passages 34 and 36. Thus, cooling fluid 30 from the reservoir 29 is pumped by the pump 31 through the fluid passage 34 to cooling fluid channel 58 of the chilled tip 42 to cool the chilled tip 42 and thus cool the tissue in contact therewith. Prior to entering the chilled tip 42, the cooling fluid 30 is at a temperature of about 5 to 20° C. The heat-absorbed cooling fluid 29 exits the chilled tip 42 via cooling fluid channel 60 at a temperature of about 20 to 50° C., and is returned to the reservoir 29 via fluid passage 36. Cooling fluid channels 58 and 60 can be considered to be part of the fluid passages 34 and 36, respectively.

Figure 4A:
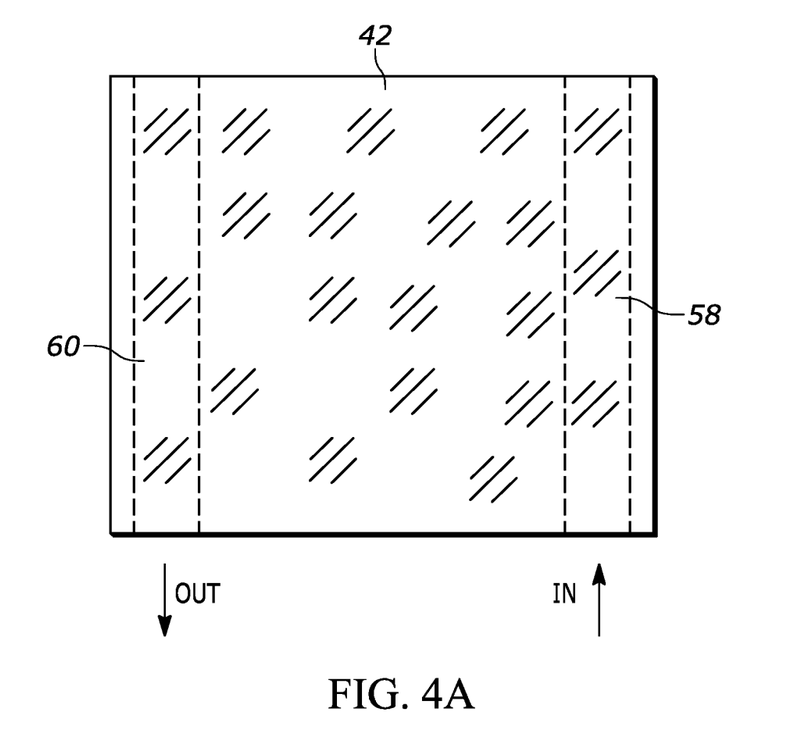
FIG. 4A is a plan view of a chilled tip including cooling fluid channels of the applicator of FIG. 3.
Figure 4B:
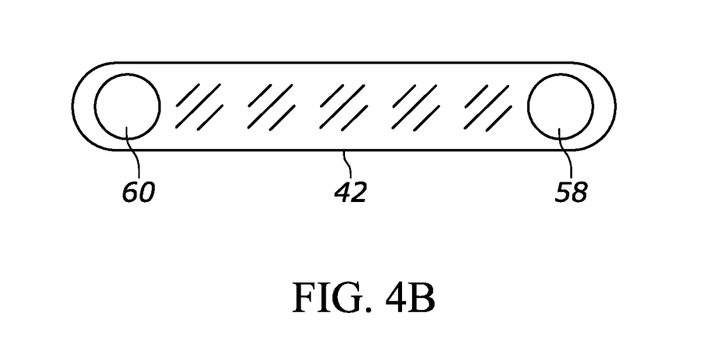
FIG. 4B is and end view of the chilled tip of FIG. 4A.

FIGS. 4A and 4B show an example of the tissue cooling element or chilled tip 42 that includes communicating cooling fluid channels 58 and 60 having generally circular cross-section. Other shapes of the channels 58, 60 can be employed such as disclosed in U.S. Patent Application No. 2017/0304645 A1, the content of which is hereby incorporated by reference into this Specification. Chilled tip 42 with cooling fluid channels 58 and 60 delivers cooled or chilled cooling fluid 30 (e.g., preferably water, but can be antifreeze) directly to and through the chilled tip 42 that is in contact with skin (see FIG. 3.) The proximity of the cooled or chilled water with the skin surface reduces the thermal resistance of the chilled tip 42. The thermal resistance just under 1 K/W is easily obtained by optimization of the chilled tip design. (In comparison for the thermoelectric cooler (TEC) cooled chilled tip designs, thermal resistances are typically around 8 K/W.) In general, the cooling fluid channels 58, 60 are positioned near to but outside of the transmitted optical path to avoid lensing affects at the interface due to unmatched refractive indices between the fluid and transparent window material.

The chilled tip 42 can be configured to include two plates, a sapphire plate for contacting the tissue 38 and a less thermally conductive glass plate with the cooling fluid 30 flowing in channel structure defined between the two plates. The glass plate minimizes condensation on top surface that faces the light source 19.

With reference to FIG. 3, a light guide 62 may be provided between the light source 19 and the chilled tip 42. The light guide 62 can be in the form of a hollow cone with mirrored walls to reflect light from the light source 19 to the chilled tip 42 and thus to the tissue 38. Alternatively, the light guide 62 can be an optical prism or waveguide. Thus, a beam L of optical energy from the light source 19 is directed through the light guide 62, through the chilled tip 42 and to the tissue 38 to irradiate the skin or tissue at area 54 defined by the chilled tip 42 being in contact with the tissue 38 on the skin treatment plane 40. The chilled tip 42 can be considered to be a portion of the light guide 62.

A cable 64 extends from proximal end 46 of the applicator housing 44 and connects the applicator 18 to the power source 20 and controller 24.

In use, applicator 18 is applied to the skin or tissue treatment plane 40 and the beam L of optical energy can be activated to apply treatment energy through the chilled tip 42 to the skin or tissue treatment plane 40. The chilled tip 42 and thus the tissue 38 in contact therewith is cooled via the cooling fluid 30 circulating through the chilled tip 42 as explained above.

Figure 5:
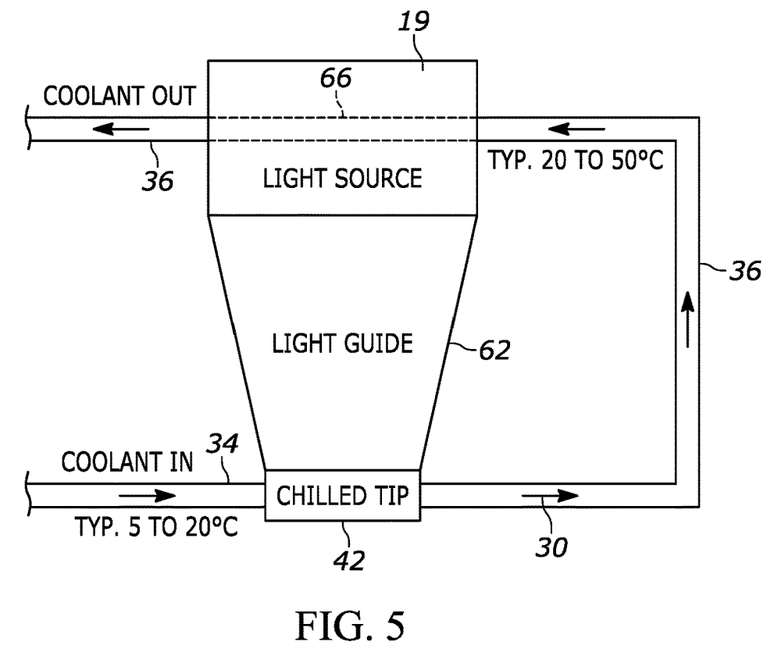
FIG. 5 is a schematic illustration showing the path of circulating cooling fluid through the chilled tip and the light source of the applicator of an embodiment.

Advantageously, in accordance with the embodiment, the two fluid passages 34, 36 can be employed to also cool the light source 19. As shown in FIG. 3 and as best shown in FIG. 5, the after the cooling fluid 30 passes through the chilled tip, fluid passage 36 is provided through or adjacent to at least a portion of the light source 19 to direct the cooling fluid 30 through or on the portion of the light source 19. If the light source 19 includes a flashlamp and laser rod, the light source 19 can sit within a bath of the cooling fluid 30 created by fluid passage 36. If the light source is a diode laser, the cooling fluid can be directed via passage 36 through small fluid channels 66 in the light source 19 to cool diode laser bars and stacks. As shown in FIG. 5, the cooling fluid 30 enters the light source at a temperature of about 20 to 50° C. Thus, the fluid passages 34 and 36 define a single cooling fluid circulation loop between the reservoir 29, the chilled tip 42 and the light source 19.

Figure 6:
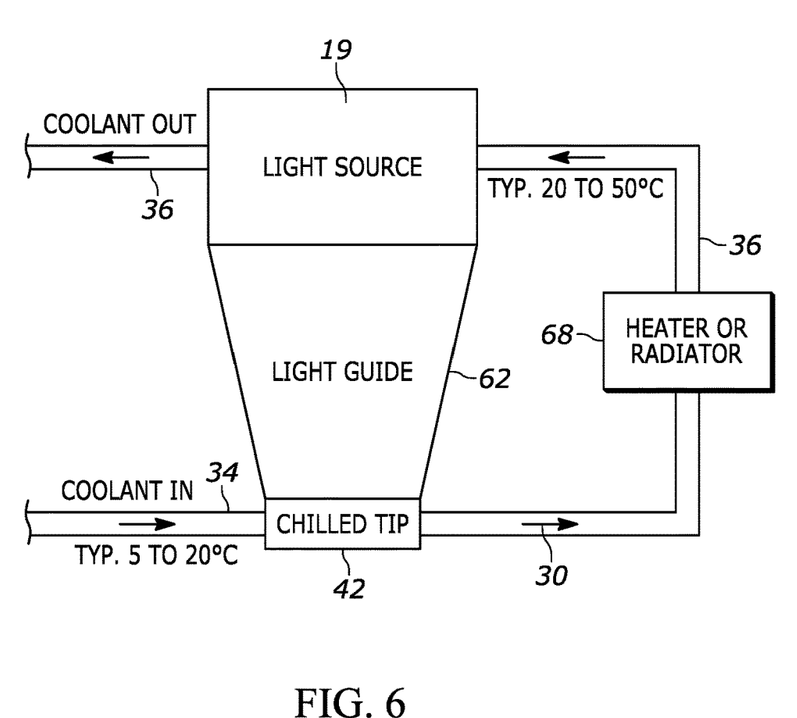
FIG. 6 is a schematic illustration showing a heater or radiator in the path of circulating cooling fluid of FIG. 5.

FIG. 6 shows another embodiment of the cooling system which is similar to the embodiment of FIG. 5, but a heat source such as a heater or radiator 68 is provided in fluid passage 36. Thus, in systems where a large temperature difference exists between tissue cooling and light source cooling, such as 5° C. for tissue cooling and 25° C. for light source cooling, the heater coil or radiator 68 can be provided to increase or control the temperature of the cooling fluid 30 before entering the light source 19.

Figure 7A:
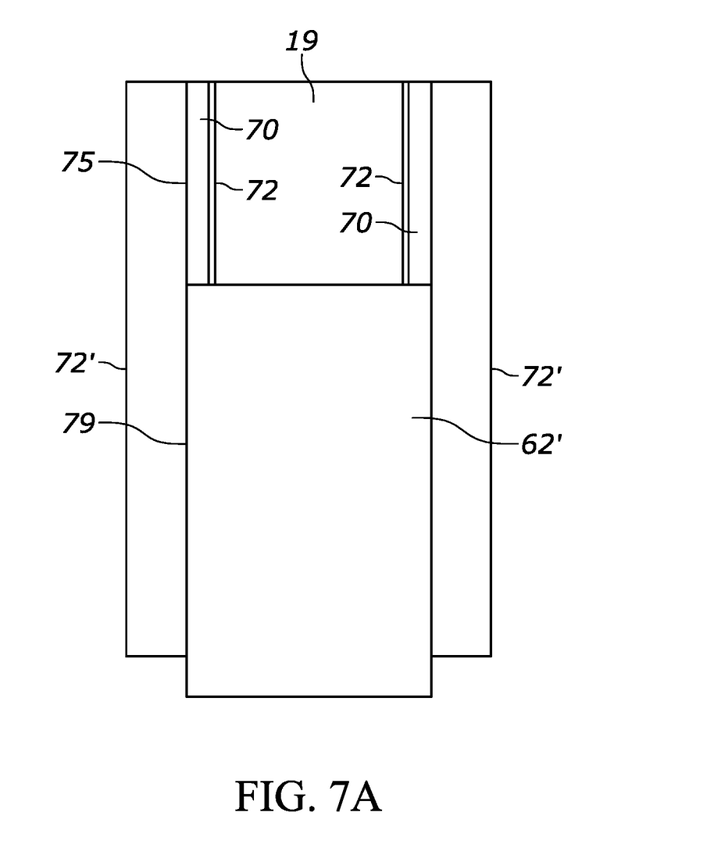
FIG. 7A is a schematic side illustration of an embodiment of the light source and light guide of the applicator, with thermoelectric coolers and cooling plates associated therewith.
Figure 7B:
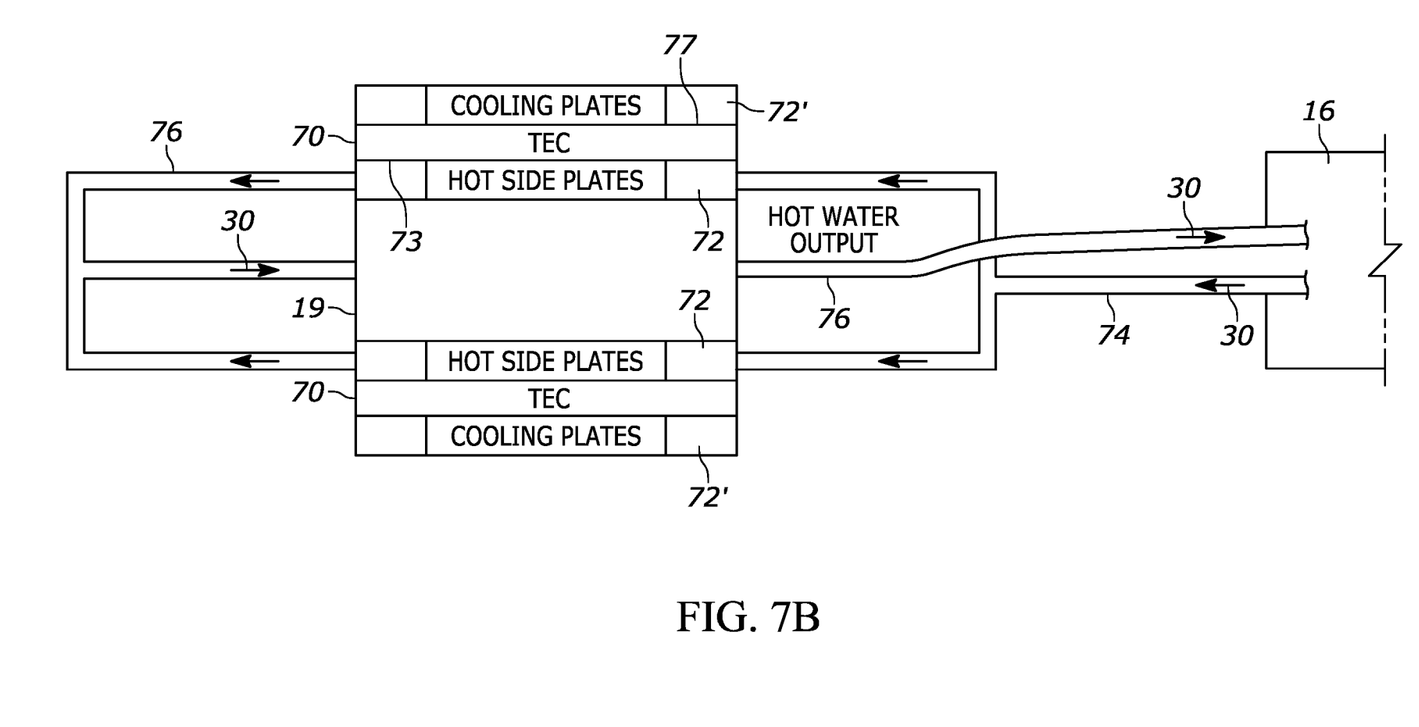
FIG. 7B is a plan view of FIG. 7A.

FIG. 7A is a side view of another embodiment of the cooling system having light source 19 and a tissue cooling element in the form of a light guide 62', preferably a waveguide in the form of a prism. No transparent window is provided. FIG. 7B is a top or plan view of FIG. 7A. A thermoelectric cooler (TEC) 70 is provided generally adjacent to at least one side of the light source 19. In the embodiment, a TEC 70 is provided generally adjacent to opposing sides of the light source. Hot side and cold side plates 72, 72' respectively, sandwich each TEC 70, with the hot side plate 72 being in contact with each side of the light source 19. Also, each hot side plate 72 is in contact with the hot side 73 of each thermoelectric cooler 70. A first portion 75 of each cold side plate 72' is mounted to the cold side 77 of the associated thermoelectric cooler 70 and a second portion 79 of each cold side plate 72' is mounted directly to the light guide 62' (FIG. 7A). With reference to FIG. 7B, cooling fluid 30 from the reservoir 29 is directed via a first fluid passage structure 74 over each hot side plate 72 to chill the cold side plates 72'. The cold side plates 72' cool the light guide 62' to cool the tissue being treated. Upon leaving the hot side plates 72, the cooling fluid is directed, via a second fluid passage structure 76, into the light source 19 to cool the light source 19. The now hotter cooling fluid 30 then exits the light source 19 and is directed back to the reservoir 29 via the second fluid passage structure 76. Similar to the embodiment of FIG. 3, a portion of each of the first and second passage structures 74 and 76 extends through the cable 16.

Figure 8:
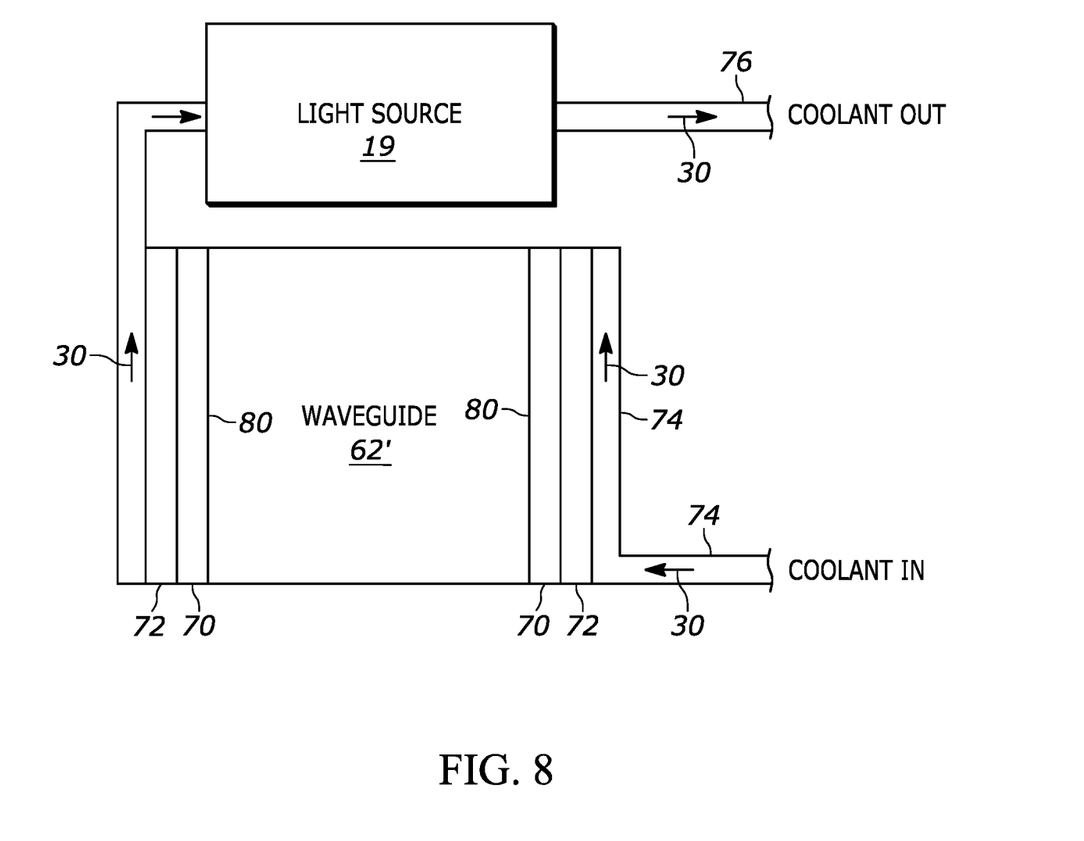
FIG. 8 is a schematic illustration of another embodiment of the light source and light guide of the applicator, with thermoelectric coolers and only hot side plates associated therewith.

FIG. 8 shows yet another embodiment for cooling the light source 19 and light guide 62'. Again, the tissue cooling element or light guide 62' is preferably a waveguide in the form of a prism. In this embodiment, no transparent window is provided and no cold side plates are provided. Instead, the cold side 80 of the TEC 70 is mounted directly onto the waveguide 62'. This configuration is more efficient compared to the use of cold side plates since there is less thermal resistance. Cooling fluid 30 is delivered from the reservoir 29 via first passage structure 74 and passes through or flows over the hot side plates 72 to cool the cold side 80 of the TEC 70 and cool the waveguide 62', and thus cool the tissue being treated. Thereafter, the cooling fluid 30 passes through the light source 19 to cool the light source. The cooling fluid 30 returns to the reservoir 29 via fluid passage structure 76. Similar to the embodiment of FIG. 7, a portion of each of the first and second passage structures 74 and 76 extends through the cable 16 (not shown in FIG. 8).

The system 10 can be employed for multiple applications but is preferably used for hair removal. For use in hair removal, the light source 19 is preferably one of a 755 nm Alexandrite laser, a semiconductor diode laser operated around 800 nm, preferably at 805 nm or 810 nm, and a 1064 nm Nd:YAG laser preferably employed to a depth of about 4 mm. Selection of the light source 19 depends on the desired type of treatment.

Thus, the tissue treatment system 10 having the cooling system of the embodiments provides an effective way to cool both the tissue 38 being treated and the light source 19 using a single delivery fluid passage 34 and a single return fluid passage 36 between the applicator 18 and cooling fluid reservoir 29. Thus, the umbilical cable 16 is not bulky and less cooling pluming is required, reducing cost.

The foregoing preferred embodiments have been shown and described for the purposes of illustrating the structural and functional principles of the present invention, as well as illustrating the methods of employing the preferred embodiments and are subject to change without departing from such principles. Therefore, this invention includes all modifications encompassed within the spirit of the following claims.

What is claimed is:

1. A tissue treatment system comprising:
   a base unit having a power source and a reservoir for containing a cooling fluid, an applicator connected with the base unit via a cable, the applicator comprising:
a tissue cooling element constructed and arranged to engage biological tissue for treatment, the tissue cooling element including channel structure associated there-with,
a light source powered by the power source and constructed and arranged to generate light energy directed to the tissue cooling element and thus to the biological tissue,
a first fluid passage between the reservoir and the channel structure of the tissue cooling element to deliver cooling fluid at a first temperature to the tissue cooling element to cool the biological tissue, such that the cooling fluid is heated to a second temperature upon heat exchange with the biological tissue, and
a second fluid passage between the channel structure and the reservoir to return the cooling fluid to the reservoir, the second fluid passage being constructed and arranged to direct the cooling fluid, at the second temperature, to the light source to cool the light source prior to being returned to the reservoir,
wherein the first and second fluid passages define a single cooling fluid circulation loop to cool both the tissue cooling element and the light source in series, and wherein a portion of each of the first and second fluid passages is disposed in the cable.

2. The system of claim 1, wherein the tissue cooling element is light guide or a transparent window.

3. The system of claim 1, wherein the cooling fluid is water or antifreeze.

4. The system of claim 1, wherein the light source is a flashlamp, a flashlamp and laser rod, or a diode laser.

5. The system of claim 1, further comprising a pump for pumping the cooling fluid from the reservoir, the system further comprising a heat exchanger constructed and arranged to keep a temperature of the cooling fluid pumped by the pump to near ambient temperature.

6. The system of claim 5, wherein the heat exchanger includes a radiator.

7. The system of claim 1, further comprising a pump for pumping the cooling fluid from the reservoir, the system further comprising a cooling module constructed and arranged to keep a temperature of the cooling fluid pumped by the pump to less than ambient temperature.

8. The system of claim 7, wherein the cooling module includes a thermoelectric cooling module or compressor refrigerator system.

9. The system of claim 1, wherein the light source is a diode laser and the second fluid passage communicates with channels in the diode laser.

10. The system of claim 1, wherein the light source includes a flashlamp and laser rod, and the light source is disposed in a bath of the cooling fluid created by the second fluid passage.

11. The system of claim 1, further comprising a heat source is provided in the second fluid passage to heat the cooling fluid prior to reaching the light source.

12. The system of claim 11, wherein the heat source is a heater or a radiator.

13. The system of claim 1, wherein the channel structure of the tissue cooling element has an inlet and the channel structure extends entirely through the tissue cooling element to an exit of the channel structure, wherein the first fluid passage is between the reservoir and the inlet of the channel structure and the second fluid passage is between the exit of the channel structure and the reservoir.

14. A tissue treatment system comprising:
a base unit having a power source and a reservoir for containing a cooling fluid,
an applicator connected with the base unit via a cable, the applicator comprising:
a light source powered by the power source and constructed and arranged to generate light energy,
a light guide disposed adjacent to the light source for directing the light energy to biological tissue, the light guide being constructed and arranged to engage the biological tissue for treatment,
at least one thermoelectric cooler having a cold side and a hot side, the cold side being associated with the light guide, and
at least one hot side plate mounted to the hot side of the thermoelectric cooler,
a first fluid passage structure between the reservoir and the hot side plate to deliver cooling fluid to the hot side plate to chill the cooling fluid to a first temperature and chill the cold side of the thermoelectric cooler and thus cool the light guide to cool the biological tissue, such that the cooling fluid is heated to a second temperature upon heat exchange with the biological tissue, and
a second fluid passage structure between the hot side plate and the reservoir to return the cooling fluid to the reservoir, the second fluid passage structure being constructed and arranged to direct the cooling fluid, at the second temperature, to the light source to cool the light source prior to being returned to the reservoir,
wherein the first and second fluid passage structures define a single cooling fluid circulation loop to cool both the light guide and the light source in series, and
wherein a portion of each of the first and second fluid passage structure is disposed in the cable.

15. The system of claim 14, wherein the light guide is a prism.

16. The system of claim 15, wherein the cold side of the thermoelectric cooler is mounted directly to the prism.

17. The system of claim 15, further comprising at least one cold side plate having a first portion mounted to the cold side of the thermoelectric cooler and a second portion mounted to the prism, the hot side plate being mounted to a portion of the light source,
wherein the first fluid passage structure is configured to deliver the cooling fluid to the hot side plate to chill the cold side of the thermoelectric cooler and the cold side plate and thus cool the light guide.

18. The system of claim 17, wherein two pairs of plates and two thermoelectric coolers are provided, each pair of plates including a cold side plate and a hot side plate with one thermoelectric cooler being disposed between associated cold side and hot side plates, the first fluid passage structure being disposed between the reservoir and each hot side plate to deliver cooling fluid to each hot side plate to chill each cold side plate and thus cool the light guide, and the second fluid passage structure being disposed between each hot side plate and the reservoir to return the cooling fluid to the reservoir, the second fluid passage structure being associated with the light source to direct cooling fluid from each hot side plate to the light source prior to being returned to the reservoir.

19. The system of claim 14, wherein the cooling fluid is water or antifreeze.

20. The system of claim 14, wherein two thermoelectric coolers and two hot side plates are provided, the first fluid passage structure being disposed between the reservoir and each hot side plate to deliver cooling fluid to each hot side plate to chill the cold side of each thermoelectric cooler and thus cool the light guide, and the second fluid passage structure being disposed between each hot side plate and the reservoir to return the cooling fluid to the reservoir, the second fluid passage structure being associated with the light source to direct cooling fluid from each hot side plate to the light source prior to being returned to the reservoir.

21. A method of cooling a tissue treatment system, the system including a base unit having a power source and a reservoir for containing a cooling fluid, an applicator connected with the base unit via a cable with the applicator including a light source powered by the power source and constructed and arranged to generate light energy, and a tissue cooling element disposed adjacent to the light source for directing the light energy to biological tissue, with a portion of the tissue cooling element being configured to contact the biological tissue, the method comprising the steps of:

provide first fluid passage structure from the reservoir and extending to be associated with the tissue cooling element, delivering the cooling fluid at a first temperature through the first passage structure to chill the tissue cooling element and thus cool the biological tissue, such that the cooling fluid is heated to a second temperature upon heat exchange with the biological tissue, providing second fluid passage structure from the tissue cooling element to the reservoir to return the cooling fluid to the reservoir, the second fluid passage structure being associated with the light source, and prior to returning the cooling fluid to the reservoir, directing the cooling fluid at the second temperature through the second passage structure to the light source to cool the light source, wherein the first and second fluid passage structures define a single cooling fluid circulation loop to cool both the tissue cooling element and the light source in series, and wherein a portion of each of the first and second fluid passage structure is disposed in the cable.

22. The method of claim 21, wherein the tissue cooling element is a transparent window or light guide including channel structure there-through, the channel structure communicating with the first and second passage structures so that the cooling fluid can flow through the channel structure.

23. The method of claim 21, wherein the tissue cooling element is a light guide in the form of a prism and the method further comprises:

providing at least one thermoelectric cooler having a hot side and a cold side, with a hot side plate being coupled to the hot side of the thermoelectric cooler and the cold side of the thermoelectric cooler being associated with the light guide, delivering the cooling fluid through the first passage structure and to the hot side plate to cool the cold side of the thermoelectric cooler and the light guide and thus cool the biological tissue.

* * * * *